United States Patent [19]

Bradshaw et al.

[11] 4,382,929
[45] May 10, 1983

[54] THIOPHENE DERIVATIVES AND THEIR PHARMACEUTICAL COMPOSITIONS AND METHOD OF USE

[75] Inventors: John Bradshaw; Duncan B. Judd, both of Ware; Barry J. Price, Hertford; John W. Clitherow, Sawbridgeworth, all of England

[73] Assignee: Glaxo Group Limited, London, England

[21] Appl. No.: 200,007

[22] Filed: Oct. 23, 1980

[30] Foreign Application Priority Data

Oct. 23, 1979 [GB] United Kingdom ............... 7936766
Feb. 29, 1980 [GB] United Kingdom ............... 8006940

[51] Int. Cl.³ .................... C07D 417/06; A61K 31/38
[52] U.S. Cl. .................... 424/246; 549/59; 549/60; 549/74; 549/75; 549/76; 424/248.51; 424/249; 424/251; 424/263; 424/267; 424/269; 424/270; 424/272; 424/274; 424/275; 544/60; 544/212; 544/146; 544/333; 546/212; 546/284; 548/266; 548/255; 548/161; 548/212; 548/233; 548/245; 548/527
[58] Field of Search ............... 544/60, 212, 146, 333; 260/326.82; 546/212, 284; 549/59, 60, 74, 75, 76; 424/248.51, 246, 267, 249, 274, 251, 263, 269, 275, 270, 272; 548/266, 255, 161, 212, 233, 245, 527

[56] References Cited

U.S. PATENT DOCUMENTS 4,239,769 12/1980 Price et al. ................ 549/75

FOREIGN PATENT DOCUMENTS 867105 11/1978 Belgium ................ 549/75

*Primary Examiner*—Robert T. Bond
*Attorney, Agent, or Firm*—Bacon & Thomas

[57] ABSTRACT

The invention provides compounds of the general formula (I)

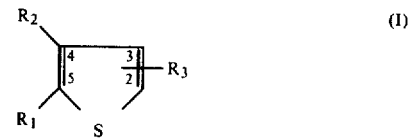

and physiologically acceptable salts, hydrates and bioprecursors thereof, in which one of $R_1$ and $R_2$ represents hydrogen, halogen or a $C_{1-4}$ alkyl group which may be optionally substituted by hydroxy or $C_{1-4}$ alkoxy, and the other represents the group $R_4R_5NAlk$— in which $R_4$ represents hydrogen, $C_{1-10}$ alkyl, cycloalkyl, alkenyl, alkynyl, aralkyl, heteroaralkyl, trifluoroalkyl, or alkyl substituted by hydroxy, alkoxy, amino, alkylamino, dialkylamino or cycloalkyl, and $R_5$ represents hydrogen or a $C_{1-4}$ alkyl group or $R_4$ and $R_5$ may, together with the nitrogen atom to which they are attached, form a 5 to 10 membered ring which may be saturated or may contain at least one double bond, may be unsubstituted or may be substituted by one or more $C_{1-3}$ alkyl groups or a hydroxy group and/or may contain another heteroatom selected from oxygen and sulphur;

Alk represents a straight or branched alkylene chain of 1 to 6 carbon atoms;

$R_3$, which may be in either the 2 or 3-position, represents the group

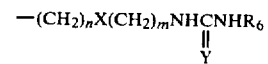

where X represents —$CH_2$—, —O— or —S—;
n represents zero, 1 or 2;
m represents 2, 3 or 4; and
where Y represents S, O, CHNO₂ or NR₇ where $R_7$ is nitro, cyano, alkylsulphonyl or arylsulphonyl;
$R_6$ represents hydrogen, alkyl, alkenyl, alkynyl, alkoxyalkyl or aralkyl;
with the provisos that
where $R_2$ represents the group $R_4R_5NAlk$ then $R_3$ is in the 2-position; and
where $R_2$ represents hydrogen then $R_3$ is in the 3-position.

The compounds of formula (I) show pharmacological activity as selective histamine $H_2$— antagonists.

10 Claims, No Drawings

THIOPHENE DERIVATIVES AND THEIR PHARMACEUTICAL COMPOSITIONS AND METHOD OF USE

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol, Chemother 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236 385. Furthermore the compounds antagonise the effect of histamine on the contraction frequency of isolated guinea pig right atrium but do not modify histamine induced contractions of isolated gastro-intestinal smooth muscle which are mediated via $H_1$-receptors.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator. Thus they may be used for example, either alone, or in combination with other active ingredients in the treatment of allergic and inflammatory conditions of the skin.

The present invention provides compounds of the general formula (I)

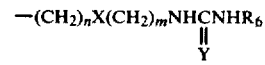

and physiologically acceptable salts, hydrates and bioprecursors thereof, in which one of $R_1$ and $R_2$ represents hydrogen, halogen or a $C_{1-4}$ alkyl group which may be optionally substituted by hydroxy or $C_{1-4}$ alkoxy, and the other represents the group $R_4R_5NAlk-$ in which $R_4$ represents hydrogen, $C_{1-10}$ alkyl, cycloalkyl, alkenyl, alkynyl, aralkyl, heteroaralkyl, trifluoroalkyl, or alkyl substituted by hydroxy, alkoxy, amino, alkylamino, dialkylamino or cycloalkyl, and $R_5$ represents hydrogen or a $C_{1-4}$ alkyl group, or $R_4$ and $R_5$ may, together with the nitrogen atom to which they are attached, form a 5 to 10 membered ring which may be saturated or may contain at least one double bond, may be unsubstituted or may be substituted by one or more $C_{1-3}$ alkyl groups e.g. methyl, or a hydroxy group and/or may contain another heteroatom, e.g. oxygen or sulphur;

Alk represents a straight or branched alkylene chain of 1 to 6 carbon atoms, preferably 1 to 4 carbon atoms;

$R_3$, which may be in either the 2- or 3-position, represents the group

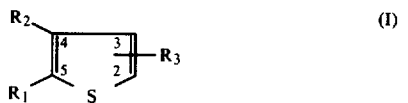

where X represents $-CH_2-$, $-O-$ or $-S-$;

n represents zero, 1 or 2;

m represents 2, 3 or 4; and where Y represents S, O, CHNO$_2$ or NR$_7$ where R$_7$ is nitro, cyano, alkylsulphonyl, or arylsulphonyl;

$R_6$ represents hydrogen, alkyl, alkenyl, alkynyl, alkoxyalkyl or aralkyl;

with the provisos that where $R_2$ represents the group $R_4R_5NAlk$ then $R_3$ is in the 2-position; and where $R_2$ represents hydrogen then $R_3$ is in the 3-position.

The term "alkyl" as a group or part of a group means that the group is straight or branched and has unless otherwise stated 1 to 6 carbon atoms, and in particular 1 to 4 carbon atoms e.g. methyl or ethyl and the terms "alkenyl" and "alkynyl" mean that the group has 3 to 6 carbon atoms. The term "cycloalkyl" means that the group has 3 to 8 carbon atoms. The term "aryl" as a group or part of a group preferably means phenyl or substituted phenyl, for example phenyl substituted with one or more $C_{1-3}$ alkyl or $C_{1-3}$ alkoxy groups or halogen atoms e.g. fluorine. The term "heteroaryl" as a group or part of a group within the definition of $R_4$, means a 5 or 6 membered monocyclic unsaturated ring which may contain one or more heteroatoms selected from oxygen, nitrogen and sulphur, e.g. furyl, pyridyl, thiazolyl or thienyl. The heteroaryl ring may be unsubstituted or substituted by $C_{1-3}$ alkyl, $C_{1-3}$ alkoxy, hydroxy, aminoalkyl, alkylaminoalkyl, dialkylaminoalkyl or halogen. The alkyl portion of a heteroaralkyl group is a straight or branched $C_{1-4}$ alkyl chain, and the heteroaryl ring is linked to the alkyl portion through either a carbon or nitrogen atom.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, tartrates, citrates, benzoates and fumarates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers. The term bioprecursors as used herein means compounds which have a structure different to that of the compounds of formula (I) but which, upon administration to an animal or human being, are converted in the body into a compound of formula (I).

The compounds according to the invention preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients. e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 2 to 4 doses to the total of some 5 mg. to 2 g per day, preferably 5 to 500 mg. per day, dependent upon the condition of the patient.

Examples of suitable meanings for the groups $R_1$, $R_2$, $R_4$, $R_5$, $R_6$, Alk and Y are as follows: hydrogen or a $R_1$ or $R_2$ (when other than the group $R_4R_5NAlk$): bromine atom or a $C_{1-3}$ alkyl group (e.g. methyl, ethyl or isopropyl) or a $C_{1-3}$ alkoxy $C_{1-3}$ alkyl group (e.g. methoxymethyl) or a hydroxy $C_{1-3}$ alkyl group (e.g. hydroxymethyl);

or, when $R_1$ or $R_2$ is the group $R_4R_5NAlk$, $R_4$: alkyl (e.g. methyl, ethyl, propyl, butyl, pentyl, hexyl, heptyl or decyl), $C_{5-7}$ cycloalkyl (e.g. cyclopentyl, cyclohexyl or cycloheptyl), alkenyl (e.g. allyl or 3,3-dimethylallyl), aralkyl (e.g. phenylalkyl such as benzyl or phenethyl), $C_{1-4}$ alkyl substituted by a trifluoromethyl group (e.g. 2,2,2-trifluoroethyl), hydroxy $C_{2-4}$ alkyl (e.g. 3-hydroxypropyl), $C_{1-3}$ alkoxy $C_{2-4}$ alkyl (e.g. methoxyethyl or ethoxyethyl), di-$C_{1-3}$ alkylaminoalkyl (e.g. dimethylaminoethyl, diethylaminoethyl or dimethylaminopropyl), or heteroaralkyl where the heterocyclic portion represents for example a furyl, thienyl, pyrrolyl, pyridinyl, pyrimidinyl, triazinyl, oxazolyl, triazolyl or thiazolyl ring and the alkylene portion is for example a methylene, ethylene or propylene grouping; and $R_5$: hydrogen or a methyl or ethyl group; or $R_4R_5N$ may represent a 5-8 membered ring optionally containing one double bond and/or substituted by one or two $C_{1-3}$ alkyl (e.g. methyl) groups or a hydroxy group and/or containing an oxygen or sulphur atom (e.g. pyrrolidino, piperidino, hexamethylenimino, heptamethylenimino, tetrahydropyridino, 4-hydroxypiperidino, 4-$C_{1-3}$ alkylpiperidino (e.g. 4-methylpiperidino), morpholino, 2,6-di-$C_{1-3}$ alkylmorpholino (e.g. 2,6-dimethylmorpholino), or thiamorpholino);

$R_6$: hydrogen, $C_{1-4}$ alkyl (e.g. methyl or ethyl) or $C_{1-3}$ alkoxy $C_{2-4}$ alkyl (e.g. methoxyethyl);

Y: $CHNO_2$ or $NR_7$ where $R_7$ is nitro, cyano, $C_{1-4}$ alkylsulphonyl (e.g. methylsulphonyl) or arylsulphonyl (e.g. phenylsulphonyl); The group Alk may be for example the group $(CH_2)_p$ where p is 1, 2, or 3. In particular the groups $R_1$, $R_2$, $R_4$, $R_5$, $R_6$, Alk and Y may have the following meanings:

$R_1$ or $R_2$ (when other than the group $R_4R_5NAlk$): hydrogen or $C_{1-4}$ alkyl (e.g. methyl);

$R_4$: $C_{1-7}$ alkyl (e.g. methyl, propyl, butyl, isobutyl or heptyl), $C_{1-4}$ alkyl substituted by a trifluoromethyl group (e.g. 2,2,2-trifluoroethyl), $C_{2-4}$ alkyl substituted by a hydroxy or di $C_{1-3}$ alkylamino group (e.g. 3-hydroxypropyl or dimethylaminoethyl), $C_{5-7}$ cycloalkyl (e.g. cyclohexyl), alkenyl (e.g. allyl), phenyl $C_{1-3}$ alkyl (e.g. benzyl), or a heteroaryl $C_{1-3}$ alkyl group where the heteroaryl ring is 5 or 6 membered and contains one heteroatom (e.g. furylmethyl);

$R_5$: hydrogen or methyl; or $R_4R_5N$ may represent a 5 to 7 membered ring, optionally containing a double bond or an alkyl (e.g. methyl) group (e.g. piperidino, 4-methylpiperidino, pyrrolidino, hexamethylenimino or tetrahydropyridino);

$R_6$: hydrogen or $C_{1-3}$ alkyl (e.g. methyl)

Y: $CHNO_2$ or $NR_7$ where $R_7$ is nitro or methylsulphonyl;

Alk is particularly a methylene or ethylene group, more particularly methylene.

When $R_3$ is in the 3-position preferably $R_2$ represents hydrogen.

When $R_3$ is in the 2-position preferably $R_2$ represents alkyl (e.g. methyl).

When X is sulphur, n is preferably 1 and m is preferably 2.

Three preferred groups of compounds are as follows:

(i) compounds in which $R_3$ is in the 3-position and $R_1$ is the group $R_4R_5NAlk$, and $R_2$ is more particularly hydrogen;

(ii) compounds in which $R_3$ is in the 2-position and $R_2$ is the group $R_4R_5NAlk$;

(iii) compounds in which $R_3$ is in the 2-position and $R_1$ is the group $R_4R_5NAlk$, and $R_2$ is more particularly alkyl (e.g. methyl).

A preferred group of compounds of formula (I) are those in which Y represents the group $CHNO_2$, and more particularly those in which $R_6$ is alkyl e.g. methyl.

A particularly preferred group of compounds of formula (I) are those of formula (II)

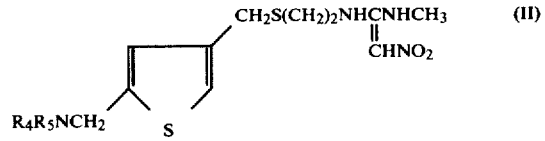

where $R_4$ and $R_5$ are methyl groups or together with the nitrogen atom to which they are attached form a pyrrolidino, piperidino or hexamethylenimino group.

The following compounds and their physiologically acceptable salts are particularly preferred:

N-methyl-N-[2[[5-(dimethylaminomethyl)-3-thienylmethyl]-thio]ethyl]-2-nitro-1,1-ethenediamine N-methyl-N'-[2-[[5-(1-pyrrolidinylmethyl-3-thienylmethyl]-thio]ethyl]-2-nitro-1,1-ethenediamine N-methyl-N'-[2-[[5-(1-piperidinylmethyl)-3-thienylmethyl]thio]ethyl]-2-nitro-1,1-ethenediamine N-[2-[[5-(dimethylaminomethyl)-4-methyl-2-thienylmethyl]-thio]ethyl]-N'-methyl-2-nitro-1,1-ethenediamine N-[2-[[5-(dimethylaminomethyl)-3-thienylmethoxy]-propyl]-N'-methyl]-2-nitro-1,1-ethenediamine.

According to one aspect the invention provides compounds of formula (I) in which one of $R_1$ and $R_2$ represents hydrogen and the other represents $R_4R_5NAlk$ and $R_3$ represents $$-(CH_2)_nX(CH_2)_m\underset{\underset{Y}{\|}}{N}HCNHR_6$$

except that Y does not represent $NR_7$ where $R_7$ is alkylsulphonyl or arylsulphonyl with the proviso that when the group $R_3$ is in the 2-position then $R_1$ represents hydrogen.

According to a further aspect the invention provides compounds of formula (I) in which $R_1$ is $R_4R_5NAlk$-, $R_2$ is halogen or a $C_{1-4}$ alkyl group which may be optionally substituted by hydroxy or $C_{1-4}$ alkoxy and $R_3$, which is in the 2-position represents $$-(CH_2)_nX(CH_2)_m\underset{\underset{Y}{\|}}{N}HCNHR_6$$

except that $R_4$ and $R_5$ do not represent alkynyl or heteroaralkyl and $R_4R_5N$ does not represent a 9 or 10 membered ring.

It will be appreciated in the methods for the preparation of the compounds of formula (I) given below, that for certain reaction steps it may be necessary to protect various reactive substituents in the starting materials for a particular reaction and subsequently to remove the protecting group. Such protection and subsequent deprotection may be particularly pertinent when $R_4$ and $R_5$ and/or $R_6$ are hydrogen. Standard protection and deprotection procedures can be employed, for example formation of phthalimide, with subsequent cleavage by treatment with a hydrazine e.g. hydrazine hydrate or a primary amine for example methylamine.

In describing the processes which may be used for preparing the compounds for formula (I) or intermediates useful in the preparation thereof, any of $R_1$ to $R_5$, Alk, X, Y, n and m are as defined in formula (I) unless otherwise stated.

Compounds of formula (I) may be made by reacting an amine of the formula $R_8NH_2$ (III) with a compound of general formula $$R_9NH\underset{\underset{Y}{\|}}{C}-P \qquad (IV)$$

wherein one of the groups $R_8$ and $R_9$ represents the group and the other represents the group $R_6$, and P is a leaving group such as halogen, thioalkyl (preferably thiomethyl) or alkoxy.

Compounds of formula (IV) may be prepared by reacting the amine (III) with a compound of formula (V)

$$P-\underset{\underset{\|}{Y}}{C}-P \qquad (V)$$

where P is as defined in formula (IV).

The above reactions may be effected in the absence or presence of a solvent e.g. ethanol, dioxan, acetonitrile, water or aqueous ethanol at a temperature from ambient to reflux. In the absence of a solvent the reaction may be carried out by heating a mixture of the reactants at for example 100°–120° C.

Compounds of formula (I) may also be prepared by treating a compound of formula (I) in which the group $R_4R_5N$ is replaced by a quaternary ammonium group (e.g. a trimethylammonium group) with an amine $R_4R_5NH$. The reaction may be carried out by heating the quaternary ammonium compound in the amine (e.g. at 100° to 120° C.) or the reaction may be carried out in the presence of a solvent such as an alkanol (e.g. ethanol) at reflux. This process is particularly applicable to compounds in which Alk is $CH_2$.

Amines of formula (III) may be made by a number of methods depending on the precise structure of the compound.

Thus amines of formula (VI)

in which n is 1 or 2 and X is oxygen or sulphur may be prepared from the corresponding alcohol of formula (VII)

in which n is 1 or 2.

For example amines of formula (VI) in which n is 1 and X is sulphur may be prepared by reacting an alcohol of formula (VII) in which n is 1 with an appropriate aminoalkane thiol salt (e.g. cysteamine hydrochloride) in a concentrated mineral acid (e.g. hydrochloric acid).

Amines of formula (VI) in which n is 2 and X is sulphur may be prepared by converting an alcohol of formula (VII) in which n is 2 into the corresponding haloalkyl compound using for example thionyl chloride or phosphorus tribromide, or mesylate by reaction with methanesulphonylchloride, followed by treatment with an appropriate aminoalkylthiol (e.g. cysteamine) in a solvent such as ethanol and in the presence of a base (e.g. sodium ethoxide).

Amines of formula (VI) in which n is 1 or 2 and X is oxygen may be prepared by treating an alcohol of formula (VII) in which n is 1 or 2 with a suitable base (e.g.

potassium t-butoxide) in a solvent (e.g. dimethylformamide) followed by the addition of an appropriate haloalkylamine (e.g. chloropropylamine).

The alcohols of formula (VII) as well as the intermediates (XIX) and (XXI) below, may be made by a variety of processes based on conventional methods in thiophene chemistry (Advances in Heterocyclic Chemistry Volume 1, 1963, page 2-116, Ed. A. R. Katritzky, Academic Press, London and New York; and Comprehensive Chemistry Volume 4, page 787, Ed. P. G. Sammes, Pergamon Press, Oxford). Some representative routes and reagents are given in each case.

Alcohols of formula (VII) in which $R_1$ is the group $R_4R_5NCH_2$, n is 1 and the hydroxymethyl substituent is in either the 2- or 3- position may be prepared by treating a compound of formula (VIII)

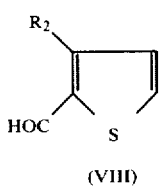 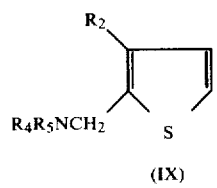

(VIII) (IX)

with an amine $R_4R_5NH$ under reducing conditions as described previously for the preparation of compounds of the invention, to give a thiophenemethanamine of formula (IX) which may be subsequently reacted with paraformaldehyde in a concentrated mineral acid (e.g. hydrochloric acid) and acetic acid to introduce the hydroxymethyl group at either the 2- or 3-position.

Alcohols of formula (VII) in which $R_2$ is the group $R_4R_5NCH_2$, n is 1 and the hydroxymethyl substituent is at the 2- position may be prepared by reacting a compound of formula (X)

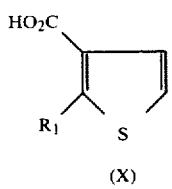 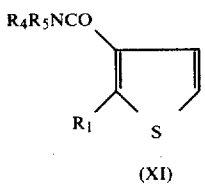

(X) (XI)

with for example oxalyl chloride in a solvent (e.g. benzene) and preferably in the presence of a catalyst (e.g. pyridine) followed by treatment with an amine $R_4R_5NH$ to give an amide of formula (XI) which is subsequently reduced with a complex metal hydride e.g. lithium aluminium hydride in a solvent such as tetrahydrofuran to give a compound of formula (XII)

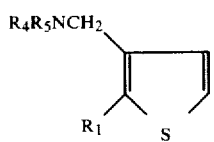

(XII)

The 2-hydroxymethyl group is then introduced by reacting the compound of formula (XII) with formaldehyde or a precursor of formaldehyde such as paraformaldehyde, in a concentrated mineral acid, e.g. hydrochloric acid or acetic acid.

Alcohols of formula (VII) in which $R_1$ is the group $R_4R_5NCH_2$, $R_2$ is hydrogen, n is 1 and the hydroxymethyl substituent is in the 3-position may be prepared from a thiophene 3-carboxylate of formula (XIII)

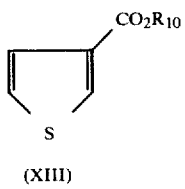 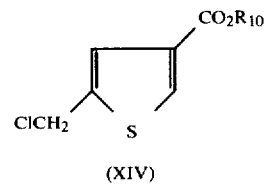

(XIII) (XIV)

where $R_{10}$ is an alkyl group. This compound is halomethylated e.g chloromethylated using for example formaldehyde, or a precursor of formaldehyde such as paraformaldehyde, and gaseous hydrogen chloride in a solvent such as chloroform and in the presence of zinc chloride to give a compound of formula (XIV). The amino group $R_4R_5N$— is then introduced into the compound of formula (XIV) by reaction with an amine $R_4R_5NH$, in a suitable solvent such as ether, to give a compound of formula (XV)

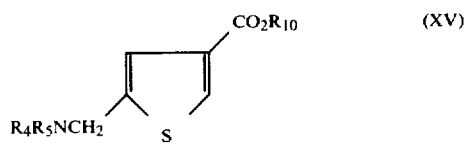

(XV)

Introduction of the 3-hydroxymethyl group is effected by reduction of the 3-carboxylate using for example lithium aluminium hydride in a suitable solvent such as ether.

Alcohols of formula (VII) in which n is 2 may be prepared by lithiating a halothiophene of formula (XVI)

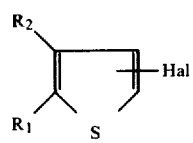 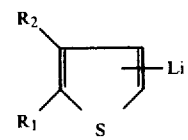

(XVI) (XVII)

(where Hal is halogen e.g. bromine) using n-butyl lithium in a suitable solvent (e.g. tetrahydrofuran) at a low temperature (e.g. $-78°$), followed by treatment of the resulting lithio derivative (XVII) with ethylene oxide in a solvent such as tetrahydrofuran, to give the desired hydroxyethyl compound (VII, n=2).

In a modification of this process a halothiophene of formula (XVI) in which $R_1$ is a group convertible to $R_4R_5NCH_2$— (e.g. an aldehyde grouping protected as an acetal) and the group Hal is at the 3-position may be lithiated and treated with ethylene oxide as described above to give a hydroxyethyl compound of formula (XVIII)

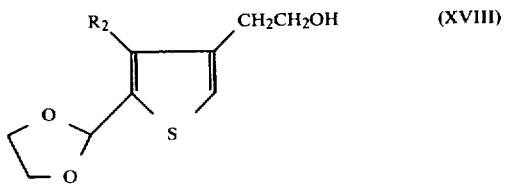

(XVIII)

Subsequent treatment with an amine $R_4R_5NH$ under reducing conditions as described previously for preparing compounds of the invention affords an alcohol of formula (VII) in which $R_1$ is the group $R_4R_5NCH_2$, n is 2 and the hydroxyethyl substituent is at the 3- position.

Amines of formula (VI) in which X is $CH_2$ may be prepared from an appropriate haloalkylthiophene of formula (XIX)

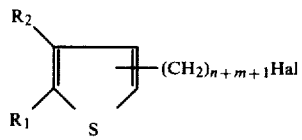
(XIX)

(in which Hal is halogen) by treatment with for example potassium phthalimide in a solvent (e.g. dimethylformamide), followed by deprotection of the phthalimido derivative using for example hydrazine hydrate.

The haloalkylthiophenes of formula (XIX) may be prepared for example by treating a lithio derivative of formula (XVII) with an α,ω- dihaloalkane (e.g. $Br(CH_2)_{n+m+1}Br$) in a solvent such as tetrahydrofuran to give an intermediate of formula (XIX).

Amines of formula (VI) in which X is $CH_2$ may also be prepared by methods involving conventional homologation of an alkyl chain. Thus for example a haloalkyl (e.g. chloroethyl) thiophene of formula (XX)

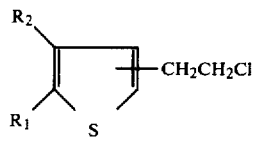
(XX)

may be treated with for example sodium cyanide in dioxan to give the corresponding cyanoethyl compound, which may then be reduced (using for example lithium aluminium hydride in tetrahydrofuran) to give the corresponding aminopropyl compound.

Alternatively a chloroethyl compound of formula (XX) may be treated with malonic ester to give, after decarboxylation, the corresponding butyric acid derivative. This may be treated with thionyl chloride for example, followed by treatment with ammonia, to give the corresponding amide which may then be reduced using for example lithium aluminium hydride to give the corresponding aminobutyl compound.

Amines of formula (VI) in which n is zero and X is oxygen may be prepared from an appropriate alkoxythiophene (XXI)

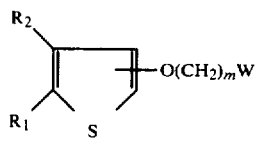
(XXI)

where W is a halogen atom (e.g. chlorine or bromine) or a leaving group (e.g. mesylate), by a similar method to that described above for the preparation of amines of formula (VI) in which X is $CH_2$ from the corresponding haloalkyl thiophene.

Alkoxythiophenes of formula (XXI) may be prepared for example by treating a halo (e.g. bromo) thiophene of formula (XVI) with a diol $HO(CH_2)_mOH$ in the presence of a base (e.g. sodium hydride) and cuprous oxide, and preferably with the addition of potassium iodide, to give a hydroxyalkoxy compound of formula (XXII)

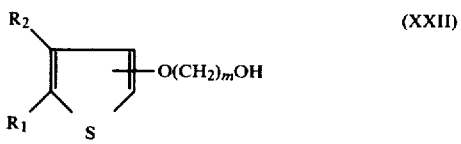
(XXII)

which may be treated with for example, thionyl chloride, phosphorus tribromide or methanesulphonyl chloride to give the alkoxythiophene of formula (XXI) in which W=halogen.

Amines of formula (VI) in which n is zero and X is sulphur may be prepared by treating a lithio derivative of formula (XVII) with elemental sulphur, followed by reaction with an appropriate haloalkylamine (e.g. chloropropylamine) preferably in protected form, e.g. as a phthalimide with subsequent cleavage of the phthalimide group using for example hydrazine hydrate.

Compounds of formula (I) and amines of formula (VI) in which Alk is an alkylene group other than $CH_2$ may be prepared from the intermediates described above in which Alk is $CH_2$ or a group convertible thereto (e.g. an ester group) by conventional means for ascending a homologous series. Thus for example a hydroxymethyl group may be converted into a chloromethyl group, which may then be converted into an aminoethyl or aminopropyl group by methods analogous to those described for amines of formula (VI) in which X is $CH_2$, and thence into the group $R_4R_5NAlk$ where Alk contains two or three methylene groups.

Where the product of any of the above processes is a free base and a salt is required, the salt may be formed in a conventional manner. Thus, for example, a generally convenient method of forming the salts is to mix appropriate quantities of the free base and the acid in an appropriate solvent(s), e.g. an alcohol such as ethanol or an ester such as ethyl acetate.

The invention is illustrated by, but not limited to, the following Examples and Preparations. In the exemplification temperatures are in °C. and t.l.c. refers to thin layer chromatography carried out on silica using one of the following solvent systems unless otherwise stated.

System A: Methanol:0.88 ammonia (79:1)

System B: Ethyl acetate:isopropanol:water:0.88 ammonia (25:15:8:2)

PREPARATION 1

(a) Methyl 5-(dimethylaminomethyl)-3-thiophene carboxylate

A solution of methyl 5-(chloromethyl)-3-thiophene-carboxylate (1.9 g) in dry diethylether (100 ml) was treated with anhydrous dimethylamine (5 ml). After 6 hours the solvent was removed in vacuo and the residue was dissolved in 5 M hydrochloric acid (20 ml). The aqueous solution was washed with diethylether, basified with 5 M sodium hydroxide (30 ml) and extracted with ether. The ethereal extracts were evaporated to give an oily residue which was distilled to yield the title compound as a colourless oil (1.6 g) b.p. 120°-130°/0.5 mm.

The picrate salt was formed in and recrystallised from ethanol m.p. 165°.

The following compounds were similarly prepared from methyl-5-(chloromethyl)-3-thiophenecarboxylate (A) and the corresponding amines:

(b) A (7 g) and pyrrolidine (10 ml) gave methyl 5-(1-pyrrolidinylmethyl)-3-thiophene carboxylate (3.3 g), Picrate salt m.p. 122°-3°.

(c) A (6 g) and piperidine (10 ml) gave methyl 5-(1-piperidinylmethyl)-3-thiophenecarboxylate (3.6 g), Picrate salt m.p. 186°.

PREPARATION 2

(a) 5-(Dimethylaminomethyl)-3-thiophenemethanol

A solution of methyl 5-(dimethylaminomethyl)-3-thiophenecarboxylate (1.5 g) in diethylether (50 ml) was treated with lithium aluminium hydride (0.21 g). After 1 hour water (2 ml) was added and the solution was filtered through diatomaceous earth. Evaporation of the filtrate gave an oily residue which distilled to give the title compound as an oil (1.2 g) b.p. (120°/0.1 mm).

The oxalate salt was formed in and recrystallised from ethanol m.p. 107°-8°.

The following compounds were similarly prepared from the corresponding ester.

(b) Methyl 5-(1-pyrrolidinylmethyl)-3-thiophenecarboxylate (3.2 g) gave 5-(1-pyrrolidinylmethyl)-3-thiophenemethanol (2.4 g). Oxalate salt m.p. 111°-2°.

(c) Methyl 5-(1-piperidinylmethyl)-3-thiophenecarboxylate (3.6 g) gave 5-(1-piperidinylmethyl)-3-thiophenemethanol (2.9 g). Oxalate salt m.p. 115°-7° C.

PREPARATION 3

Methyl 5-(hydroxymethyl)-3-thiophenecarboxylate

A solution of methyl 5-(chloromethyl)-3-thiophenecarboxylate (1.7 g) in 50% aqueous acetone (60 ml) was treated with silver nitrate (1.52 g). After 2 h the resulting precipitate was filtered and the filtrate was evaporated. The residue was extracted with diethyl ether, and the ethereal extract was washed with water. Evaporation of the solvent gave an oily residue, which was chromatographed on silica with ethyl acetate-light petroleum 60°-80°; (1:1) to give the title compound as an oil (0.3 g) b.p. 110/0.1 mm m.p. 38°-40°.

PREPARATION 4

5-(Hydroxymethyl)-N,N-dimethyl-3-thiophenecarboxamide

A mixture of methyl 5-(hydroxymethyl)-3-thiophenecarboxylate (3 g), sodium methoxide (0.2 g) and excess anhydrous dimethylamine in dry methanol (20 ml) was stirred for 24 h at ambient temperature. The solvent was removed in vacuo, water was added and the product was extracted with ethyl acetate. The organic extract was evaporated to leave an oily residue which was chromatographed on silica with ethyl acetate-light petroleum 40°-60°; (1:1) to give the title compound (1.3 g). I.R. (CHBr$_3$) OH 3,595 cm$^{-1}$; C=O 1,620 cm$^{-1}$

PREPARATION 5

4-(Dimethylaminomethyl)-2-thiophenemethanol

A solution of 5-(hydroxymethyl)-N,N-dimethyl-3-thiophenecarboxamide (1.7 g) in dry tetrahydrofuran (150 ml) was treated with a 0.5 M solution of aluminium hydride in tetrahydrofuran (26 ml). After 2 h at room temperature, water (5 ml) was cautiously added and the mixture was filtered through diatomaceous earth. The filtrate was evaporated to leave an oily residue, which was dissolved in 2 M hydrochloric acid (20 ml). The aqueous solution was washed with diethyl ether, basified with 5 M sodium hydroxide and extracted with ethyl acetate.

The organic extract was distilled to give the title compound as an oil (1 g) b.p. 110/0.1 mm I.R. (CHBr$_3$) OH 3585 cm$^{-1}$; Me$_2$NCH$_2$ 2,775 cm$^{-1}$ and 2,820 cm$^{-1}$

PREPARATION 6

1-(3-Methyl-2-thienylmethyl)piperidine

A mixture of 3-methyl-2-thiophenecarboxaldehyde (20 g), formic acid (6 ml) and N-formyl piperidine (44.4 ml) was heated under reflux for 12 h. Water (50 ml) and 2 M hydrochloric acid (30 ml) were added; and the aqueous solution was washed with ether. The solution was basified to pH 10 with 2 M sodium hydroxide (30 ml) and extracted with ether. The organic extract was evaporated to give a brown oil which was distilled to afford the title compound as a colourless oil (11.8 g) b.p. 70°/0.4 mm. NMR (CDCl$_3$) 2.9,d, (1H); 3.27,d, (1H); 6.48,s, (2H); 7.6,m, (4H); 7.83,s, (3H); ca. 8.5,m, (>6H).

PREPARATION 7

5-(Dimethylaminomethyl)-4-methyl-2-thiophenemethanol

A solution of N,N,3-trimethyl-2-thiophenemethaneamine (1.5 g) in dry tetrahydrofuran (50 ml) was treated with a solution of n-butyl lithium (1.6 M; 7 ml) at room temperature, under nitrogen. After 4 h, gaseous formaldehyde (excess) was added and the mixture was heated at 40° C. for 20 h.

Water (100 ml) and chloroform (100 ml) were added and the organic solution evaporated in vacuo to leave an oily residue which was dissolved in ethanol (50 ml) and treated with sodium borohydride (0.1 g), followed by acetic acid (10 ml). The reaction mixture was evaporated to dryness and the residue was dissolved in sodium carbonate solution (8%, 50 ml) and extracted with chloroform. The organic extract was distilled to give the title compound as a colourless oil (0.65 g) b.p. 120°/0.1 mm.

The oxalate salt was formed in and recrystallised from a mixture of ethanol and ethyl acetate m.p. 116°-7° C.

(b) Similarly, 1-(3-methyl-2-thienylmethyl)piperidine (3 g) gave 4-methyl-5-(1-piperidinylmethyl)-2-thiophenemethanol as an oil (2.4 g) b.p. 120°/0.2 mm.

N.m.r. (CDCl$_3$) 3.32,s,(1H); 5.32,s,(2H); 6.48,s,(2H); 7.38,brs,(1H);

7.50-7.7,m,(4H); 7.89,s,(3H); 8.30-8.80,m,(6H).

PREPARATION 8

(a)

4-[[2-(Amino)ethyl]thio]methyl-N,N-dimethyl-2-thiophenemethanamine

A mixture of 5-(dimethylaminomethyl)-3-thiophenemethanol (1 g) and 2-aminoethanethiol hydrochloride (0.67 g) was stirred in concentrated hydrochloric acid (7 ml) at 0° C. for 2 hours; and then at room temperature for 48 hours. Solid anhydrous sodium carbonate was added and the product was extracted into ethyl acetate.

The organic extract was distilled to give the title compound as a colourless oil (0.75 g) b.p. 130°/0.05 mm. The oxalate salt was formed in ethanol and recrystallised from ethanol and water m.p. 178°-9°.

The following compounds were similarly prepared from 2-aminoethanethiol hydrochloride (A) and the corresponding thiophenemethanol.

(b) A (1.5 g) and 5-(1-pyrrolidinylmethyl)-3-thiophenemethanol (2.4 g) gave 2[[4-(1-pyrrolidinylmethyl)-2-thienylmethyl]thio]ethanamine (1.4 g). Oxalate salt m.p. 162°–4°.

(c) A (1.6 g) and 5-(1-piperidinylmethyl)-3-thiophenemethanol (2.9 g) gave 2-[[4-(1-pyrrolidinylmethyl)-2-thienylmethyl]thio]ethanamine (2.2 g), Oxalate salt m.p. 89°–91°.

(d) A (0.65 g) and 4-(dimethylaminomethyl)-2-thiophenemethanol (0.9 g) gave 5-[[2-aminoethyl]thio]-methyl-N,N-dimethyl-3-thiophenemethanamine (0.8 g) b.p. 130°/0.1 mm. Oxalate salt m.p. 151°–2°.

(e) A (0.6 g) and 5-(dimethylaminomethyl)-4-methyl-2-thiophenemethanol (0.6 g) gave 5-[[2-aminoethyl]thio]methyl-N,N,3-trimethyl thiophenemethanamine as a colourless oil (0.69 g) g.p. 150°/0.1 mm. Oxalate salt m.p. 212° dec.

(f) A (1.11 g) and 4-methyl-5-(1-piperidinylmethyl)-thiophene-2-methanol (2.2 g) gave 2-[[4-methyl-5-(1-piperidinylmethyl)-2-thienylmethyl]thio]ethanamine as a yellow viscous oil (1.88 g) b.p. 170°/0.05 mm.

(g) A (1.2 g) and 4-(1-pyrrolidinylmethyl)-2-thiophenemethanol (1.7 g) gave 2[[4-(1-pyrrolidinylmethyl)-2-thienylmethyl]-thio]ethanamine. b.p. 165°/0.02 mm. Oxalate salt m.p. 147°–8°.

(h) A (1.3 g) and 5-methyl-4-(dimethylaminomethyl)-2-thiophenemethanol (2 g) gave 5-[[2-(aminoethyl)]thio]methyl-N,N,2-trimethyl-3-thiophenemethanamine (1.9 g). Oxalate salt m.p. 146°–7°.

PREPARATION 9

4-(1-Pyrrolidinylmethyl)-2-thiophenemethanol
1-(3-Thienylcarbonyl) pyrrolidine

A mixture of 3-thiophenecarboxylic acid (15 g) oxalylchloride (15 ml) and pyridine (0.05 ml) in toluene (100 ml) was heated at reflux for 2 hours. The excess reagent was removed in vacuo and the toluene solution was added to a solution of dry pyrrolidine (25 ml) in dry toluene (100 ml). After 2 h the reaction mixture was washed with dilute hydrochloric acid, 8% aqueous sodium carbonate, saturated brine and water. The organic solution was dried and evaporated to give the title compound (1.8 g) as a white crystalline solid m.p. 70°–73°.

1-(3-Thienylmethyl)pyrrolidine

A solution of 1-(3-thienylcarbonyl) pyrrolidine (12 g) in dry diethylether (200 ml) was added to a slurry of lithium aluminium hydride (2.6 g) in dry diethylether (100 ml). The mixture was stirred for 1 hour, and aqueous 5 M sodium hydroxide (20 ml) was added. The mixture was filtered and the filtrate was distilled to give the title compound (9.8 g) as a colourless oil. b.p. 120/15 mm.

4-(1-Pyrrolidinylmethyl)-2-thiophenemethanol

A solution of paraformaldehyde (1.5 g) in conc. hydrochloric acid (15 ml) and acetic acid (30 ml) was treated with 1-(3-thienylmethyl)pyrrolidine (2.7 g); and the mixture was stirred for 18 hours, at room temperature.

The mixture was poured onto saturated aqueous sodium carbonate and extracted with chloroform. The chloroform solution was extracted with dilute hydrochloric acid. The aqueous extract was basified with anhydrous sodium carbonate and extracted with chloroform. The chloroform extract was dried and evaporated to give an oil which was purified firstly by thin layer chromatography on silica with a mixture of ethyl acetate:ethanol:0.88 ammonia (40:3:2) as eluant, and finally by distillation to give the title compound (0.8 g) as a colourless oil. b.p. 140/0.02 mm.

PREPARATION 10

5-(Dimethylaminomethyl)-3-thiophenemethanol

Methyl
5-[(dimethylamino)carbonyl]-3-thiophenecarboxylate

A mixture of methyl 3-thiophenecarboxylate (2.8 g) and N,N-dimethylcarbonyl chloride (2.0 ml) was treated with stannic chloride for 5 minutes and the mixture was stirred for 20 hours. Chloroform and iced water were added. The organic solution was washed with 8% aqueous sodium carbonate, dried and evaporated to give a viscous oil. This oil was heated at 70° in vacuo and the residue was dissolved in methyl acetate. Petroleum ether was added to give the title compound (1.1 g) as a crystalline solid m.p. 51°–2° C.

5-(Dimethylaminomethyl)-3-thiophenemethanol

A solution of methyl 5-[(dimethylamino)carbonyl]-3-thiophenecarboxylate (0.5 g) in dry diethylether (50 ml) was added to a slurry of lithium aluminium hydride (0.3 g) in dry diethylether (100 ml). The mixture was stirred for 3 hours at room temperature. Water was cautiously added, the mixture was filtered and the filtrate was evaporated to give the title compound (0.4 g) as a colourless oil b.p. 120°/0.1 mm. The oxalate was formed in and recrystallised from ethanol m.p. 107°–8°.

PREPARATION 11

5-Methyl-4-(dimethylaminomethyl)-2-thiophenemethanol N,N,3-trimethyl-3-thiophene carboxamide A mixture of 2-methyl-3-thiophene carboxylic acid (2 g) and oxalyl chloride (2 ml) in dry toluene (20 ml) was heated under reflux and was treated with pyridine (0.05 ml). The reaction mixture was heated at reflux for 1 h, cooled and partially evaporated. The residue was added to a solution of dimethylamine in toluene at 0° to 5° C. After 2 hours water and diethyl ether were added. The organic phase was washed with dilute hydrochloric acid, sodium hydroxide and water, dried and evaporated to an oil which was distilled to give the title compound (1.4 g) as a colourless oil b.p. 100°/0.1 mm.

N,N,2-Trimethyl-3-thiophenemethanamine

A solution of N,N,3-trimethyl-3-thiophene carboxamide (1.3 g) in dry diethylether (50 ml) was added to a slurry of lithium aluminium hydride (0.3 g) in dry diethylether (100 ml) at room temperature. The mixture was stirred for 1 hour and then water was added. The mixture was filtered and the filtrate was evaporated to give the title compound (0.75 g) as a colourless oil. The picrate salt was formed in ethanol m.p. 155°.

5-Methyl-4-(dimethylaminomethyl)-2-thiophenemethanol

A mixture of N,N,2-trimethyl-3-thiophenemethanamine (6.1 g), paraformaldehyde (3.0 g) in conc. hydrochloric acid (20 ml) and acetic acid (45 ml) was stirred at 0° to 5° C. for 1 hour, and at 8° for 72 hours. The mixture was added to an ice-cold, saturated solution of sodium carbonate. Aqueous 5 M sodium hydroxide was added and the mixture was stirred for 20 hours. The solution was extracted with chloroform and the organic extract was washed with dilute sodium hydroxide and saturated brine, dried and evaporated to leave an oil. This residue was distilled to give the title compound (6 g) as a pale yellow oil b.p. 120°/0.1 mm. The oxalate salt was formed in ethanol and ethyl acetate m.p. 129°–131° C.

PREPARATION 12

3-[5-(Dimethylaminoethyl)-3-thiophenemethoxy]-propanamine dioxalate salt

To a solution of 5-(dimethylaminomethyl)-thiophene-3-methanol (5.2 g) and potassium tertiarybutoxide (3.4 g) in dry dimethylformamide (100 ml) was added 3-chloropropylamine hydrochloride (7.8 g) in dimethylformamide (10 ml). The mixture was stirred at 20° for 3 h. A further portion of potassium tertiarybutoxide (6.8 g) was added followed by 3-chloropropylamine hydrochloride (7.8 g) in dimethylformamide (10 ml) and the reaction was stirred at 20° for 18 h. The mixture was concentrated in vacuo, tetrahydrofuran (100 ml) was added followed by potassium carbonate and the mixture was filtered. The filtrate was concentrated, and purified by column chromatography on silica using methanol and methanol: ammonia (79:1) to give an oil (2.2 g). Addition of oxalic acid to a solution of oil in ethanol gave the title compound as an off-white solid, m.p. 176°–178° (d).

PREPARATION 13

4-[3-(Amino)propoxy]-N,N,-dimethyl-2-thiophenemethanamine

4-Bromo-N,N-dimethyl-2-thiophenemethanamine

A mixture of 4-bromo-2-thiophenecarboxaldehyde (4.8 g), dry dimethylformamide (4.3 ml) and 98% formic acid (1.4 ml), was heated at 120° for 30 h. The cooled mixture was poured into water (100 ml) and basified with anhydrous sodium carbonate. Diethyl ether (2×100 ml) was added and the ethereal solution was extracted with dilute hydrochloric acid (50 ml). The aqueous solution was basified with anhydrous sodium carbonate and extracted with diethyl ether (200 ml). The ethereal extracts were distilled to give the title compound (2.5 g) as a colourless oil, b.p. 70°/0.1 mm.

3-[5-(Dimethylaminomethyl)-3-thienyloxy]-1-propanol

A mixture of 1,3-propanediol (20 ml) and sodium hydride (1 g) was stirred at 80° for 1 h. Copper (II) oxide (1.3 g), sodium iodide (0.05 g) and 4-bromo-N,N-dimethyl-2-thiophenemethanamine (5 g) were added and heating was continued for 2 days. Dilute hydrochloric acid (60 ml) was added and the aqueous solution was washed with diethyl ether (50 ml), basified with aqueous sodium hydroxide and extracted with chloroform (200 ml). The organic extract was distilled to give the title compound (1.7 g) as an off-white wax. m.p. 32°–4°

3-[5-(Dimethylaminomethyl)-3-thienyloxy]-1-propanol methanesulphonate hydrochloride A solution of 3-[5-(dimethylaminomethyl)-3-thienyloxy]-1-propanol (0.25 g) and methanesulphonyl chloride (0.1 ml) in dry dichloromethane (10 ml) at 0°–5° was stirred for 1 h. The mixture was poured onto an ice cold 4% aqueous solution of sodium carbonate (50 ml). The solution was extracted with dichloromethane (20 ml). The organic extract was evaporated to give the title compound (0.05 g) as a white solid.

I.r. (Nujol) 2,550; 2,450, 1,350, 1,170 and 1,195 cm$^{-1}$
N.m.r. (CDCl$_3$) of base: 3.40,brs(1H); 3.82,d,(1H); 5.62,t,(2H); 5.98,t,(2H); 6.50,s,(2H); 7.01,s,(3H); 7.75–7.80,s+m,(8H).

2-[3-[[5-(Dimethylaminomethyl)-3-thienyloxy]propyl]]-(1H)-isoindole-1,3-(2H) dione A solution of 3-[5-(dimethylaminomethyl)-3-thienyloxy]-1-propanol methanesulphonate hydrochloride (6 g) in dichloromethane (200 ml) was washed with dilute sodium hydroxide (50 ml). The organic solution was dried (Na$_2$SO$_4$), filtered and evaporated leaving an oil. This oil was dissolved in dry dimethylformamide (100 ml), and potassium phthalimide (3.7 g) was added. The mixture was stirred for 72 h. The excess solvent was removed in vacuo and the residue was dissolved in diethylether (1 l) was washed with water (2 l). The ethereal solution was dried (Na$_2$SO$_4$), filtered and evaporated to give the title compound (4.8 g) as an amber oil.

I.r. (CHBr$_3$) 2,780, 2,820, 1,770, 1,710 cm$^{-1}$

4-[3-(Amino)propoxy]-N,N-dimethyl-2-thiophenemethanamine

A solution of 2-[3-[[5-(dimethylaminomethyl)-3-thienyloxy]propyl]]-(1H)-isoindole-1,3(2H)-dione (4.6 g) was dissolved in a 30% solution of methylamine in ethanol (100 ml). The mixture was stirred at room temperature for 4 h and heated on a steam-bath for 2 h. The solvent was evaporated and the residue was dissolved in dilute hydrochloric acid (20 ml). The aqueous solution was basified with anhydrous sodium carbonate, washed with diethyl ether (150 ml) and extracted with toluene (200 ml). The toluene solution was distilled to give the title compound (1.6 g) as a colourless oil, b.p. 120°/0.06 mm.

The oxalate salt was formed in and recrystallised from ethanol and water m.p. 150°–2°.

PREPARATION 14

5-[(3-Aminopropyl)thio]-N,N,3-trimethyl-2-thiophenemethanamine

N-[3-[[5-Dimethylamino)methyl-4-methyl-2-thienyl]-thio]propyl]-isoindole-1,3(2H)-dione A solution of N,N,3-trimethyl-2-thiophenemethanamine (6.2 g) in dry tetrahydrofuran (100 ml) was treated with a solution of n-butyl lithium in hexane (1.6 M, 27.5 ml) at 0°, under nitrogen. After 1 h, sulphur (1.4 g) was added. After a further 0.5 h a solution of N-(3-bromopropyl)-isoindole-1,3(2H)-dione (11.8 g) in dry tetrahydrofuran (50 ml) was added and the mixture was stirred at room temperature for 18 h. Water (100 ml) was added and the mixture extracted with ether. The organic extract was evaporated to give the title compound as a yellow oil (15.3 g).

I.r. (CHBr$_3$) 2820, 2775, 1770, 1705, 1392 cm$^{-1}$

5-[(3-Aminorpopyl)thio]-N,N,3-trimethyl-2-thiophenemethanamine

N-[3-[[5-(Dimethylamino)methyl-4-methyl-2-thienyl]thio]propyl]isoindole-1,3(2H)-dione (15.2 g) and hydrazine hydrate (8 ml) were stirred at room temperature in tetrahydrofuran (150 ml) for 48 h. The mixture was filtered and the filtrate was distilled to give the title compound as an orange oil (6.9 g), b.p. 160°–170°/0.04 mm.

EXAMPLE 1

(a)

N-Methyl-N-[2-[[5-dimethylaminomethyl]-3-thienylmethyl]thio]ethyl-2-nitro-1,1-ethenediamine A mixture of 4-[[2-(amino)ethyl]thio]methyl-N,N-dimethyl-2-thiophene methanamine (0.35 g) and N-methyl-1-(methylthio)-2-nitroethenamine (0.23 g) in water (5 ml) was stirred at room temperature for 24 hours. The resulting precipitate was collected by filtration and recrystallised from methanol and water to give the title compound as an off-white solid (0.27 g) m.p. 143°.

Assay found: C, 47.3; H, 6.7; N, 16.8%. $C_{13}H_{22}N_4O_2S_2$ requires: C, 47.3. H, 6.7; N, 17.0%.

The following compounds were similarly prepared from N-methyl-1-(methylthio)-2-nitroethenamine [A] and the appropriate diamine.

(b) A (0.45 g) and 2-[[4-(1-pyrrolidinylmethyl)-2-thienylmethyl]thio]ethanamine (0.75 g) gave N-Methyl-N'-[2-[[5-(1-pyrrolidinylmethyl)-3-thienylmethyl]thio]ethyl]-2-nitro-1,1-ethenediamine (0.72 g), m.p. 128°–130°.

Assay found: C, 50.4; H, 6.7; N, 15.15; $C_{15}H_{24}N_4O_2S_2$ requires: C, 50.5; H, 6.8; N, 15.7%.

(c) A (0.23 g) and 5-[[2-(amino)ethyl]thio]methyl-N,N-dimethyl-3-thiophenemethanamine (0.35 g) gave N-methyl-N-[2-[[4-(dimethylaminomethyl)-2-thienylmethyl]thio]ethyl]-2-nitro-1,1-ethenediamine, carbonate salt as a white solid (0.2 g) m.p. 99°–100°.

Assay found: C, 44.93; H, 6.46; N, 15.45. $C_{13}H_{22}N_4O_2S_2 \cdot \frac{1}{2}H_2CO_3$ requires: C, 44.85; H, 6.41; N, 15.50%.

(d) A (0.28 g) and 2-[[5-(1-piperidinylmethyl)-3-thienylmethyl]thio]ethanamine (0.5 g) gave N-methyl-N'-[2-[[5-(1-piperidinylmethyl)-3-thienylmethyl]thio]ethyl]-2-nitro-1,1-ethenediamine as a white solid (0.4 g) m.p. 101°–3°.

Assay found: C, 51.93; H, 7.03; N, 15.09; $C_{16}H_{26}N_4O_2S_2$ requires: C, 51.87; H, 7.02; N, 15.13%.

(e) A (0.2 g) and 5-[[[2-(amino)ethyl]thio]methyl]-N,N,3-trimethylthiophenemethanamine (0.3 g) gave N-[2-[[5-Dimethylaminomethyl)-4-methyl-2-thienylmethyl]thio]ethyl]N'-methyl-2-nitro-1,1-ethenediamine (which was purified by column chromatography on silica using methanol as eluant) as a white solid (0.38 g) m.p. 82°–3°.

Assay found: C, 48.6; H, 7.0; N, 15.9. $C_{14}H_{24}O_2S_2$ requires: C, 48.8; H, 7.0; N, 16.3%.

(f) A (0.27 g) and 2-[[4-methyl-5-(1-piperidinylmethyl)-2-thienylmethyl]thio]ethanamine (0.5 g) gave N-methyl-N'-[2-[[4-methyl-5-(1-piperidinylmethyl)-2-thienylmethyl]-thio]ethyl]-2-nitro-1,1-ethenediamine as a white solid, recrystallised from methyl acetate-light petroleum b.p. 60°–80° (1:3), (0.1 g) m.p. 81°.

Assay found: C, 53.11; H, 7.38; N, 14.52. $C_{17}H_{28}N_4O_2S_2$ requires: C, 53.11; H, 7.34; N, 14.58%.

(g) A (0.25 g) and 2-[[4-(1-pyrrolidinylmethyl)-2-thienylmethyl]thio]ethanamine (0.4 g) gave N-Methyl-N'-[2-[[4-(1-pyrrolidinylmethyl)-2-thienylmethyl]thio]ethyl]-2-nitro-1,1-ethenediamine as a white solid (0.25 g) m.p. 109°–111°.

Assay found: C, 50.25; H, 6.75; N, 15.4. $C_{15}H_{24}N_4O_2S_2$ requires: C, 50.55; H, 6.8; N, 15.7.

(h) A (0.26 g) and 5-[[2-(amino)ethyl]thio]methyl-N,N,2-trimethyl-3-thiophenemethanamine (0.4 g) gave N-Methyl-N'-2-[[4-(dimethylaminomethyl)-5-methyl-2-thienylmethyl]thio]ethyl]-2-nitro]-1,1-ethenediamine as a white solid (0.25 g) m.p. 100°–101°.

Assay found: C, 48.65; H, 6.85; N, 16.10 $C_{14}H_{24}N_4O_2S_2$. requires: C, 48.80; H, 7.0; N, 16.25.

(i) A (0.27 g) and 3-[5-(dimethylaminomethyl)-3-thiophenemethoxy]propanamine (0.4 g) gave N-[2-[[5-(dimethylaminomethyl)-3-thienylmethoxy]propyl]-N'-methyl-2-nitro-1,1-ethenediamine (0.42 g) as a pale orange oil.

T.l.c. System B Rf 0.43

N.M.R. (CDCl$_3$) 0,0,br,(1H); 3.9,br,(1H); 2.88,s,(1H); 3.12,s,(1H); 3.45,s,(1H); 5.59,s,(2H); 6.3,m,(2H); 6.43,s,(2H); 6.7,m,(2H); 7.40,d,(3H); 7.75,s,(6H); 8.08,m,(2H);

(j) A (0.35 g) and 4-[3-(amino)propoxy]-N,N-dimethyl-2-thiophenemethanamine (0.5 g) gave N-[3-[5-(dimethylaminomethyl)-3-thienyloxy]propyl]-N'-methyl-2-nitro-1,1-ethenediamine (0.35 g), which was purified by column chromatography and crystallised from methyl acetate m.p. 113°.

N.m.r. (CDCl$_3$)—0.4,brs,(1H); 3.40,brs,(3H); 3.82,d,(1H); 6.00,t,(2H); 6.50–6.55,s+brs,(4H); 7.1,brs,(3H); 7.75–7.9,s+m,(8H).

(k) A (0.4 g) and 5-[(3-aminopropyl)thio]-N,N,3-trimethyl-2-thiophenemethanamine gave N-[3-[[5-dimethylamino)methyl-4-methyl-2-thienyl]thio]propyl]-N'-methyl-2-nitro-1,1-ethenediamine which was purified by column chromatography as a light brown oil (0.353 g).

N.m.r. (CDCl$_3$):—0.25 br.s (1H); 3.18,s,(1H); 3.4,br.s,(1H) overlain by 3.4,s,(1H); 6.53 s,(2H); 6.55,q,(2H); 7.1,m,(3H), 7.18,t,(2H); 7.72,s,(6H); 7.9,s,(3H); 8.05,m,(2H).

Found: C, 48.8; H, 7.0; N, 16.2; $C_{14}H_{24}N_4O_2S_2$ requires: C, 48.8; H, 7.1; N, 15.8%.

EXAMPLE 2

N-[[[2-[[5-(Dimethylaminomethyl)-3-thienylmethyl]thio]ethyl]amino](methylamino)methylene]methanesulphonamide A mixture of 4-[[2-(amino)ethyl]thio]methyl-N,N-dimethyl-2-thiophenemethanamine (0.4 g) and S,S'-dimethyl-N-(methylsulphonyl)-dithio-carbonimidic acid (0.35 g) in ethanol (10 ml) was heated at 60° C. for 1 hour. A 33% solution of methylamine in ethanol (10 ml) was added and the mixture was stirred for 20 h. The solvent was evaporated in vacuo and the residue was purified by column chromatography on silica using methanol to give the title compound (0.5 g) as an amber gum.

Assay found: C, 41.0; H, 6.6; N, 14.7. $C_{13}H_{24}N_4O_2S_3$ requires: C, 40.8; H, 6.9; N, 14.5%.

N.m.r. (CDCl$_3$): 2.9, s, (1H); 3.09, s, (1H); 3.25, brs, (1H); 4.30, brs. (1H); 6.28, s, (2H); 6.39, s, (2H); 6.61, q, (2H); 7.08, s, (3H); 7.16, d, (3H); 7.36, t, (2H); 7.73, s, (6H).

EXAMPLE 3

N[11]-Cyano-N-[2-[[5-[(dimethylamino)methyl]-4-methyl-2-thienylmethyl]thio]ethyl]-N[1]-methylquanidine 5-[[2-(Amino)ethyl]thio]methyl-N,N,3-trimethylthiophenemethanamine (0.5 g) and methyl N-cyano-N'-methylcarbonimidothioate (0.27 g) were heated at 110°–130° in vacuo for 7 h. The resulting mixture was purified by column chromatography on silica using methanol to give the title compound as a brown oil (0.35 g).

T.l.c. System A Rf. 0.52

N.m.r. (CDCl$_3$) 3.57,s,(1H); 4.16,br,q,(1H); 4.55,br,t,(1H); 6.17,s,(2H); 6.52,s,(2H); 6.63,q,(2H); 7.17,s,(3H); 7.30,t,(2H); 7.75,s,(6H); 7.9,s,(3H).

Examples of Pharmaceutical Compositions

TABLETS:

|  | mg/tablet |
|---|---|
| Active ingredient | 100.00 |
| Microcrystalline Cellulose BPC | 198.50 |
| Magnesium stearate BP | 1.50 |
| Compression weight | 300.00 |

The active ingredient is sieved through a 250 μm sieve, blended with the excipients and compressed using 9.5 mm punches. Tablets of other strengths may be prepared by altering the compression weight and using punches to suit.

The tablets may be film coated with suitable film forming materials, e.g. methyl cellulose or hydroxypropyl methyl cellulose using standard techniques. Alternatively the tablets may be sugar coated.

Injection for Intravenous Administration

|  | % w/v |
|---|---|
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of formula (I)

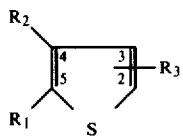

(I)

and physiologically acceptable salts and hydrates thereof, in which one of R$_1$ and R$_2$ represents hydrogen, halogen or a C$_{1-4}$ alkyl group which may be optionally substituted by hydroxy or C$_{1-4}$ alkoxy, and the other represents the group R$_4$R$_5$Nalk- in which R$_4$ represents hydrogen, C$_{1-10}$ alkyl, C$_{3-8}$ cycloalkyl, C$_{3-6}$ alkenyl, C$_{3-6}$ alkynyl, ar C$_{1-6}$ alkyl wherein ar is phenyl or phenyl substituted with one or more C$_{1-3}$ alkyl or C$_{1-3}$ alkoxy groups or halogen atoms; heteroaralkyl wherein the heteroaryl portion is a furyl, thienyl, pyrrolyl, pyridinyl, pyrimidinyl, triazinyl, oxazolyl, triazolyl or thiazolyl ring which may be unsubstituted or substituted by C$_{1-3}$ alkyl, C$_{1-3}$ alkoxy, hydroxy, amino C$_{1-6}$ alkyl, C$_{1-6}$ alkylamino C$_{1-6}$ alkyl, di C$_{1-6}$ alkylamino C$_{1-6}$ alkyl or halogen, and the alkyl portion of the heteroaralkyl group is a straight or branched C$_{1-4}$ alkyl chain, and the heteroaryl ring is linked to the alkyl portion through a carbon or nitrogen atom; trifluoro C$_{1-6}$ alkyl, or C$_{1-6}$ alkyl substituted by hydroxy, C$_{1-6}$ alkoxy, amino, C$_{1-6}$ alkylamino, di C$_{1-6}$ alkylamino or C$_{3-8}$ cycloalkyl, and R$_5$ represents hydrogen or a C$_{1-4}$ alkyl group or R$_4$ and R$_5$ may, together with the nitrogen atom to which they are attached form a pyrrolidino, piperidino, hexamethylenimino, heptamethylenimino, tetrahydropyridino, morpholino or thiamorpholino group which may be unsubstituted or may be substituted by one or more C$_{1-3}$ alkyl groups or a hydroxy group;

Alk represents a straight or branched alkylene chain of 1 to 6 carbon atoms;

R$_3$, which may be in either the 2- or 3- position, represents the group

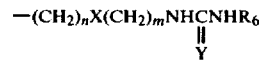

where X represents —CH$_2$—, —O— or —S—;
n represents zero, 1 or 2;
m represents 2, 3 or 4; and
where Y represents S, O, CHNO$_2$ or NR$_7$ where R$_7$ is nitro, cyano, C$_{1-6}$ alkylsulphonyl or arylsulphonyl wherein aryl is phenyl or phenyl substituted with one or more C$_{1-3}$ alkyl or C$_{1-3}$ alkoxy groups or halogen atoms;
R$_6$ represents hydrogen, C$_{1-6}$ alkyl, C$_{3-6}$ alkenyl, C$_{3-6}$ alkynyl, C$_{1-6}$ alkoxy C$_{1-6}$ alkyl or ar C$_{1-6}$ alkyl, wherein ar is phenyl or phenyl substituted with one or more C$_{1-3}$ alkyl or C$_{1-3}$ alkoxy groups or halogen atoms;
with the provisos that
where R$_2$ represents the group R$_4$R$_6$NAlk then R$_3$ is in the 2- position; and
where R$_2$ represents hydrogen then R$_3$ is in the 3- position.

2. A compound according to claim 1, in which the groups R$_1$, R$_2$, R$_4$, R$_5$, R$_6$, Alk and Y have the following meanings:

R$_1$ or R$_2$ (where other than the group R$_4$R$_5$NAlk): hydrogen or a bromine atom or a C$_{1-3}$ alkyl group or a C$_{1-3}$ alkoxy C$_{1-3}$ alkyl group or a hydroxy C$_{1-3}$ alkyl group; or when R$_1$ or R$_2$ is the group R$_4$R$_5$NAlk R$_4$: C$_{1-10}$ alkyl, C$_{5-7}$ cycloalkyl, C$_{3-6}$ alkenyl, ar C$_{1-6}$ alkyl, wherein ar is phenyl or phenyl substituted with one or more C$_{1-3}$ alkyl or C$_{1-3}$ alkoxy groups or halogen atoms; C$_{1-4}$ alkyl substituted by a trifluoromethyl group, hydroxy C$_{2-4}$ alkyl, C$_{1-3}$ alkoxy C$_{2-4}$ alkyl, di C$_{1-3}$ alkylamino C$_{1-3}$ alkyl, or heteroaralkyl where the heteroaryl portion represents a furyl, thienyl, pyrrolyl, pyridinyl, pyrimidinyl, triazinyl, oxazolyl, triazolyl or thiazolyl ring and the alkylene portion is a methylene, ethylene or propylene grouping; and R$_5$: hydrogen or a methyl or ethyl group; or R$_4$R$_5$N: is pyrrolidino, piperidino, hexamethylenimino, heptamethylenimino, tetrahydropyridino, morpholino or a thiamorpholino group which may be substituted by one or two C$_{1-3}$ alkyl groups or a hydroxy group;

R$_6$: hydrogen, C$_{1-4}$ alkyl or C$_{1-3}$ alkoxy C$_{2-4}$ alkyl;

Y: CHNO$_2$ or NR$_7$ where R$_7$ is nitro, cyano, or C$_{1-4}$ alkylsulphonyl, or arylsulphonyl, wherein the aryl portion is phenyl or phenyl substituted with one or more C$_{1-3}$ alkyl or C$_{1-3}$ alkoxy groups or halogen atoms; Alk represents the group $(CH_2)_p$ where p is 1, 2 or 3.

3. A compound to claim 1 in which $R_3$ is in the 3-position and $R_1$ is the group $R_4R_5NAlk$.

4. A compound according to claim 1 in which $R_3$ is in the 2-position and $R_1$ is the group $R_4R_5NAlk$.

5. A compound according to claim 1 in which Alk is methylene.

6. A compound according to claim 1 in which Y represents the group $CHNO_2$.

7. A compound according to claim 1 corresponding to formula (II),

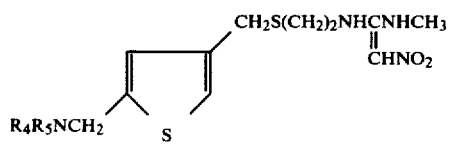

(II)

where $R_4$ and $R_5$ are methyl groups or together with the nitrogen atom to which they are attached form a pyrrolidino, piperidino or hexamethylenimino group.

8. A compound according to claim 1 which are: N-methyl-N-[2[[5-(dimethylaminomethyl)-3-thienylmethyl]thio]ethyl]-2-nitro-1,1-ethenediamine  N-methyl-N'-[2-[[5-(1-pyrrolidinyl methyl)-3-thienylmethyl]thio]ethyl]-2-nitro-1,1-ethenediamine  N-methyl-N'-[2-[[5-(1-piperidinylmethyl)-3-thienylmethyl]thio]ethyl]-2-nitro-1,1-ethenediamine  N-[2-[[5-(dimethylaminomethyl)-4-methyl-2-thienylmethyl]thio]ethyl]-N'-methyl-2-nitro-1,1-ethenediamine N-[2-[[5-dimethylaminomethyl]-3-thienylmethoxy]-propyl]-N'-methyl-2-nitro-1,1-ethenediamine, and their physiologically acceptable salts.

9. A method of treating a condition mediated through histamine $H_2-$ receptors which comprises administering to a patient an effective amount of a compound according to claim 1 to relieve said condition.

10. A pharmaceutical composition for the treatment of conditions mediated through $H_2$-receptors comprising an effective amount of at least one compound as claimed in claim 1 together with at least one pharmaceutically acceptable carrier or diluent.

* * * * *